(12) United States Patent
Scott

(10) Patent No.: US 12,059,340 B2
(45) Date of Patent: Aug. 13, 2024

(54) BREAST IMPLANT WITH POSITION MARKER

(71) Applicant: Susan Scott, Merritt Island, FL (US)

(72) Inventor: Susan Scott, Merritt Island, FL (US)

( * ) Notice: Subject to any disclaimer, the term of this patent is extended or adjusted under 35 U.S.C. 154(b) by 229 days.

(21) Appl. No.: 17/652,795

(22) Filed: Feb. 28, 2022

(65) Prior Publication Data

US 2022/0175515 A1 Jun. 9, 2022

Related U.S. Application Data

(63) Continuation of application No. 16/782,448, filed on Feb. 5, 2020, now Pat. No. 11,259,913.

(60) Provisional application No. 62/801,812, filed on Feb. 6, 2019.

(51) Int. Cl.
*A61F 2/12* (2006.01)

(52) U.S. Cl.
CPC ........ *A61F 2/12* (2013.01); *A61F 2250/0098* (2013.01)

(58) Field of Classification Search
CPC ............................ A61F 2/12; A61F 2250/0098
See application file for complete search history.

(56) References Cited

U.S. PATENT DOCUMENTS

| 6,203,570 | B1* | 3/2001 | Baeke | A61F 2/12 |
| | | | | 623/7 |
| 11,259,913 | B2* | 3/2022 | Scott | A61F 2/12 |
| 2003/0074084 | A1* | 4/2003 | Nakao | A61F 2/12 |
| | | | | 623/8 |
| 2004/0254438 | A1* | 12/2004 | Chuck | A61B 5/0084 |
| | | | | 604/9 |
| 2006/0229721 | A1* | 10/2006 | Ku | A61L 27/18 |
| | | | | 623/8 |
| 2011/0098576 | A1* | 4/2011 | Hollstien | A61B 5/4851 |
| | | | | 600/476 |
| 2012/0302874 | A1* | 11/2012 | Hollstien | A61B 5/0084 |
| | | | | 600/476 |
| 2014/0200396 | A1* | 7/2014 | Lashinski | A61B 17/0401 |
| | | | | 600/37 |
| 2017/0296273 | A9* | 10/2017 | Brown | A61B 6/4441 |
| 2017/0367809 | A1* | 12/2017 | Glicksman | A61F 2/12 |
| 2019/0142574 | A1* | 5/2019 | Quirós | A61F 2/12 |
| | | | | 623/8 |
| 2019/0240052 | A1* | 8/2019 | Chen | A61F 5/0033 |
| 2020/0085526 | A1* | 3/2020 | Schuessler | A61F 2/12 |
| 2020/0129258 | A1* | 4/2020 | Feinberg | A61B 90/02 |
| 2020/0352704 | A1* | 11/2020 | Schuessler | A61F 2/12 |
| 2021/0169504 | A1* | 6/2021 | Brown | A61B 6/487 |

* cited by examiner

*Primary Examiner* — Suzette J Gherbi

(74) *Attorney, Agent, or Firm* — Dunlap Bennett & Ludwig, PLLC

(57) ABSTRACT

A breast implant includes an outer shell made of a polymer and a filler material disposed within the outer shell. At least one opaque marking is disposed on the outer shell. The opaque marker is visible through the skin when a light emitter emits light through the chest tissue. This allows a user to determine if the breast implant is flipped or rotated based on the location of the opaque marker.

1 Claim, 2 Drawing Sheets

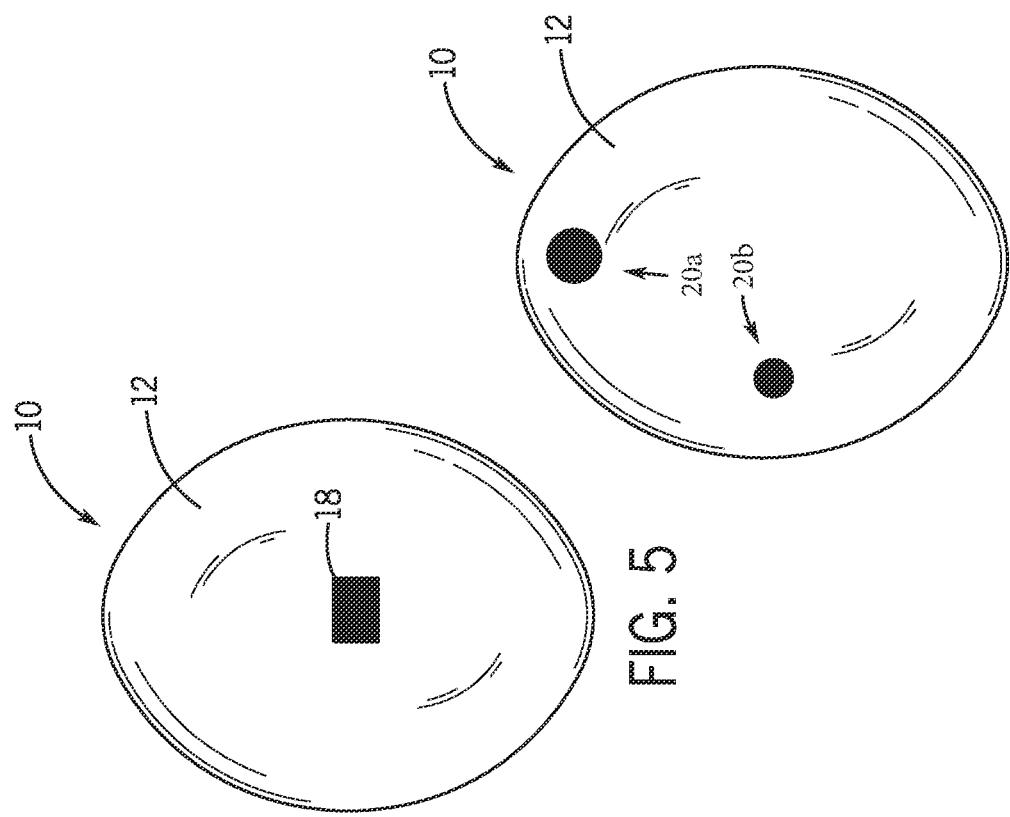
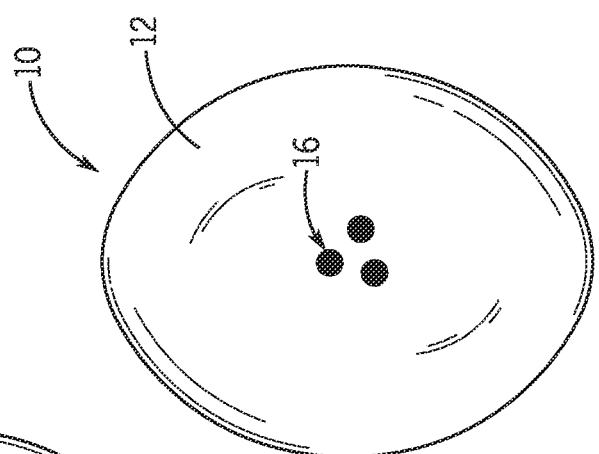
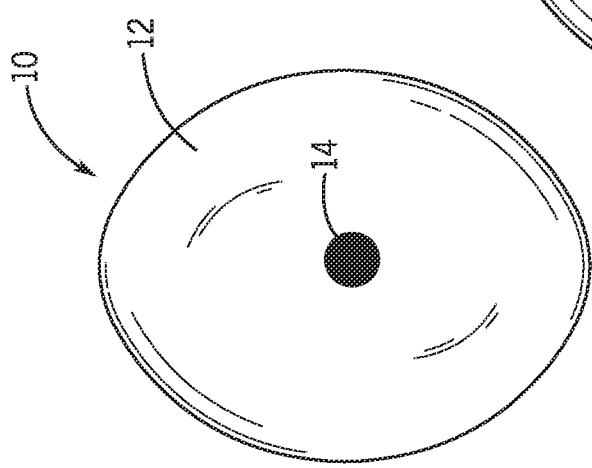

BREAST IMPLANT WITH POSITION MARKER

CROSS-REFERENCE TO RELATED APPLICATION

This application claims the benefit of priority of (1) U.S. provisional application No. 62/801,812, filed Feb. 6, 2019, and (2) U.S. non-provisional application Ser. No. 16/782,448, filed Feb. 5, 2020, the contents of both of which are herein incorporated by reference.

BACKGROUND OF THE INVENTION

The present invention relates to breast implants and, more particularly, to a breast implant with a position marker.

Mastectomy is the medical term for the surgical removal of one or both breasts. A mastectomy is usually carried out to treat breast cancer. In some cases, people believed to be at high risk of breast cancer have the operation as a preventive measure.

A breast implant is a prosthesis used to change the size, shape, and contour of a person's breast. In reconstructive plastic surgery, breast implants can be placed to restore a natural looking breast following a mastectomy or to correct congenital defects and deformities of the chest wall. The implant is placed either under or over the pectoralis major muscle.

Mastectomies require removal of all breast tissue. For women who have had mastectomies, breast implants tend to move around underneath the chest skin because of the absence of breast tissue. For example, a woman who sleeps on their side or stomach may experience breast implants rotating or flipping overnight. When a breast implant rotates or flips, it may not readily be apparent to the individual. Because nerves are cut during a mastectomy there is no sensation to alert a woman of implant malposition.

As can be seen, there is a need for a system and method of detecting when a breast implant has rotated or flipped.

SUMMARY OF THE INVENTION

In one aspect of the present invention, a breast implant comprises: an outer shell made of a polymer; and a filler material disposed within the outer shell, wherein at least one opaque marking is disposed on the outer shell.

In another aspect of the present invention, a method of determining if a breast implant is displaced comprises steps of: implanting a breast implant underneath the chest skin of a human body, the breast implant comprising: an outer shell made of a polymer, and a filler material disposed within the outer shell, wherein at least one opaque marking is disposed on the outer shell; and placing a light emitter against the chest skin of the human body, wherein at least one opaque marking is visible through the chest skin when light from the light emitter is shining through the chest skin, and a location of at least one opaque marking indicates if the breast implant is displaced within the human body.

In yet another aspect of the present invention, the breast implant includes the following: an outer shell made of a polymer; a first opaque marking disposed at a first position of a periphery of the outer shell; and a second opaque marking disposed at a second position of a periphery of the outer shell, wherein the first position is near a medial plane of the outer shell, wherein the second position is near a lateral plane of the outer shell, wherein the first position is a medial position relative to the outer shell, wherein the second position is a lateral position relative to the outer shell, wherein the outer shell comprises a flat rear surface and a rounded front surface, wherein the first position is disposed on the rounded front surface, wherein the first position is disposed on the rounded front surface, wherein the second position is disposed on the rounded front surface, wherein the second position is disposed on the flat rear surface, wherein the first position is disposed on the flat rear surface, wherein the second position is disposed on the flat rear surface, or wherein the second position is disposed on the rounded front surface.

These and other features, aspects and advantages of the present invention will become better understood with reference to the following drawings, description and claims.

BRIEF DESCRIPTION OF THE DRAWINGS

FIG. 3 is a front view of an embodiment of the present invention;

FIG. 4 is a front view of an embodiment of the present invention;

FIG. 5 is a front view of an embodiment of the present invention; and

FIG. 6 is an elevation view of an embodiment of the present invention, illustrating a first opaque marking 20*a* along a medial plane of the outer shell and a second opaque marking 20*b* along a lateral plane of the outer shell, and it being understood that the opaque markings 20*a* and 20*b* may be along the flat rear surface or the round front surface.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Figure 2:
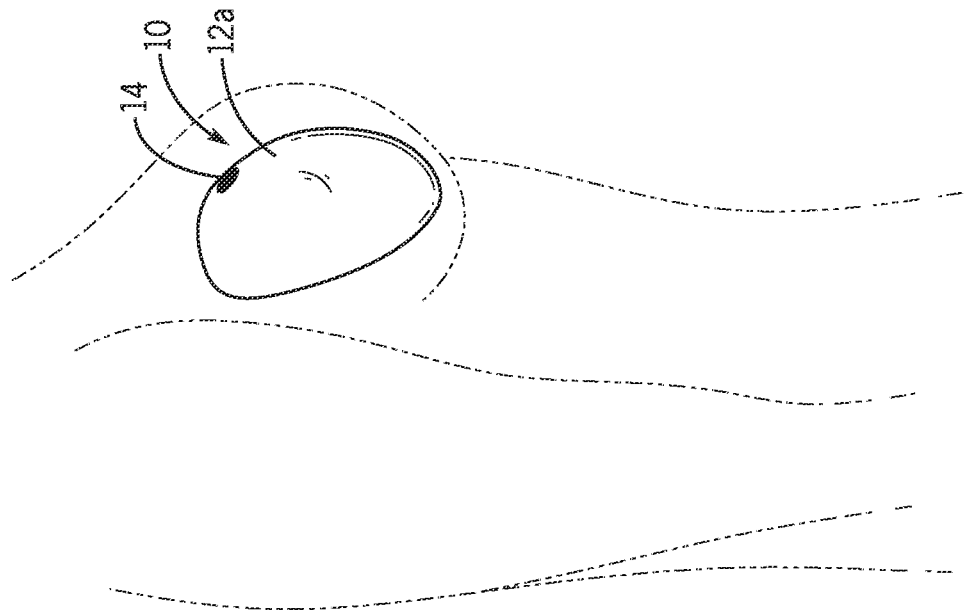
FIG. 2 is a side perspective view of an embodiment of the present invention, shown in use and in an undesired orientation.
Figure 1:
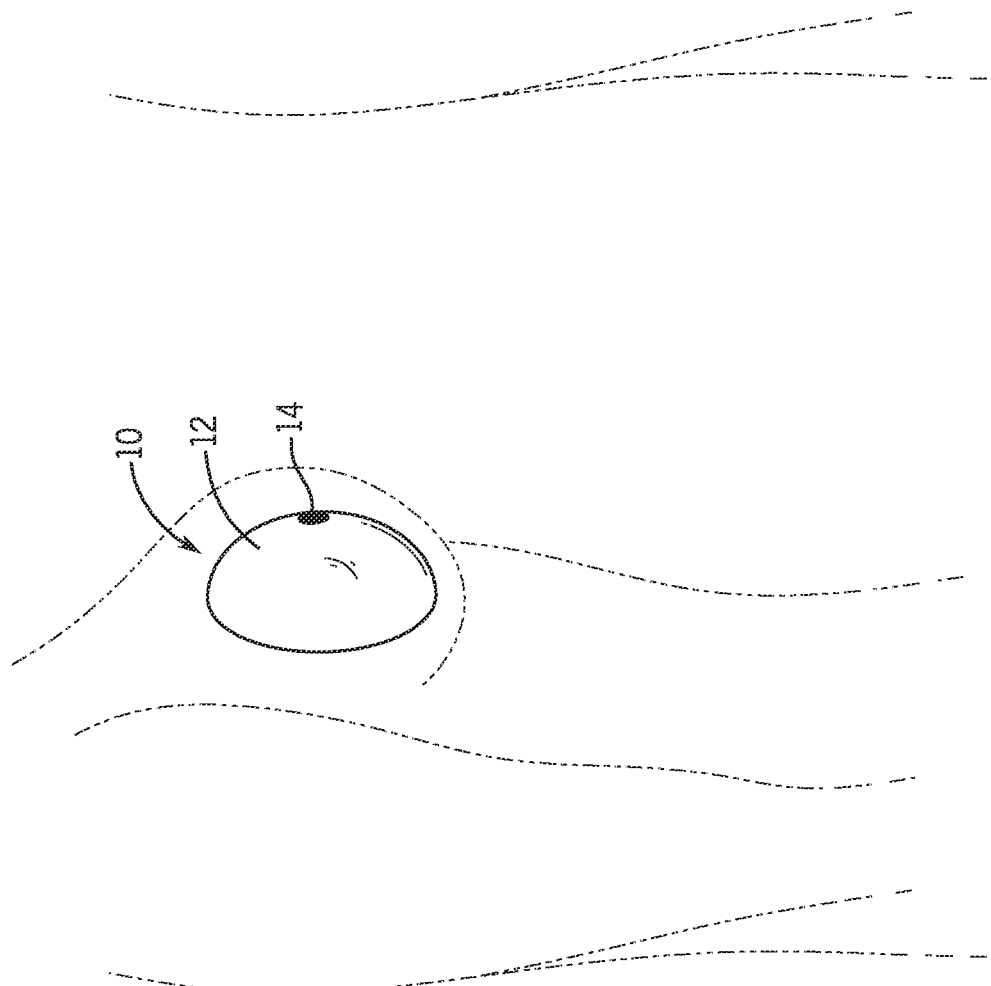
FIG. 1 is a side perspective view of an embodiment of the present invention, shown in use and in a desired orientation.

Referring to FIGS. 1 through 6, the present invention includes a breast implant. The breast implant includes an outer shell 10 made of a polymer and a filler material 12 disposed within the outer shell 10. At least one opaque marking 14 is disposed on the outer shell 10. The opaque marker 14 is visible through the skin when a light emitter emits light through the chest tissue. This allows a user to determine if the breast implant is flipped or rotated based on the location of the opaque marker 14.

As mentioned above, the breast implant includes an outer shell 10 and a filler material 12 disposed within the outer shell 10. The outer shell may be made of an elastomer silicone or any material that may be used as an outer shell for a breast implant. The filler material 12 may be a saline solution, a viscous silicone gel, or any filler that may be used as a filler material for a breast implant. The outer shell 10 may include a flat rear surface and a rounded front surface. For example, the outer shell 10 may include a tear drop shape or a dome shape.

The opaque marking 14 of the present invention may be printed on an outer surface of the breast implant. The opaque marking 14 is a dark color and allows little or no light to pass through. For example, the opaque marking 14 may be black, brown, or other dark color. As illustrated in FIGS. 3 through 5, the opaque marking 14 may be disposed at a central portion of the rounded front surface. The opaque marking 14 may be circular, square 18, dotted 16, or other shape or pattern. The opaque marking 14 being disposed at a central portion of the rounded front surface allows a user to determine if the breast implant has flipped from front to back.

As illustrated in FIG. 6, the present invention may include a first opaque marking 20a and a second opaque marking 20b. The first opaque marking 20a may be distinguishable from the second opaque marking 20b. For example, the first opaque marking 20a may be larger than the second opaque marking 20b. Alternatively, the first opaque marking 20a and the second opaque marking 20b may be a different shape or pattern. The first opaque marking 20a may be disposed at a first position of a periphery of the rounded front surface and the second opaque marking 20b may be disposed at a second position of a periphery of the rounded front surface.

Since the first opaque marking 20a and the second opaque marking 20b are distinguishable and located at different positions along the periphery of the rounded front surface, a user may determine if the breast implant has rotated along an x-axis, y-axis, z-axis, or a combination thereof. For example, the first opaque marking 20a may be located at a twelve o'clock position on the rounded front surface and the second opaque marking 20b may be located at a nine o'clock position on the rounded front surface. Alternatively, the first opaque marking 20a and the second opaque marking 20b may be located at different positions along the periphery. This allows a user to observe whether the breast implant has flipped on its side, flipped from top to bottom, or rotated clockwise or counterclockwise.

A method of determining if a breast implant is displaced may include steps of: implanting a breast implant underneath a chest skin of a human body, the breast implant having: an outer shell made of a polymer, and a filler material disposed within the outer shell, wherein at least one opaque marking is disposed on the outer shell; and placing a light emitter against the chest skin of the human body. Then at least one opaque marking is visible through the chest skin when light from the light emitter is shining through the chest skin, especially in an area with low or little light. A location of the at least one opaque marking indicates if the breast implant is displaced within the human body. As for the example in FIG. 6, the first opaque marking 20a is located at a twelve o'clock position on the rounded front surface and the second opaque marking 20b is located at a nine o'clock position on the rounded front surface when the breast implant is in a correct position within the human body. When the first opaque marking 20a and the second opaque marking 20b are displaced from the above-mentioned position, the breast implant is displaced and needs to be repositioned.

It should be understood, of course, that the foregoing relates to exemplary embodiments of the invention and that modifications may be made without departing from the spirit and scope of the invention as set forth in the following claims.

What is claimed is:

1. A method of determining if a breast implant is displaced comprising steps of:
   implanting a breast implant underneath a chest skin of a human body, wherein, when implanted, the breast implant comprises:
      an outer shell made of a polymer;
      a first opaque marking disposed at a first position on a central portion of a front portion of a periphery of the outer shell; and
      a second opaque marking disposed at a second position of the periphery of the outer shell; and
   placing a light emitter against the chest skin of the human body, wherein the first and second opaque markings are visible through the chest skin when light from the light emitter is shining through the chest skin in such a way that a location of the first and second opaque markings indicates if the breast implant is displaced within the human body, wherein the first opaque markings provides, via visual inspection, an indication of a flipping, from front to back, of the breast implant.

* * * * *